(12) United States Patent
Aujla

(10) Patent No.: US 10,285,752 B2
(45) Date of Patent: May 14, 2019

(54) MULTILAYER SPLIT ABLATION ELECTRODE

(71) Applicant: Biosense Webster (Israel) Ltd., Yokneam (IL)

(72) Inventor: Vishav Manak Singh Aujla, Valencia, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 460 days.

(21) Appl. No.: 14/960,779

(22) Filed: Dec. 7, 2015

(65) Prior Publication Data

US 2017/0156784 A1 Jun. 8, 2017

(51) Int. Cl.
| | |
|---|---|
| *A61B 18/12* | (2006.01) |
| *A61B 18/14* | (2006.01) |
| *G01K 7/02* | (2006.01) |
| *A61B 17/00* | (2006.01) |
| *A61B 18/00* | (2006.01) |
| *A61B 90/00* | (2016.01) |

(52) U.S. Cl.
CPC .......... *A61B 18/14* (2013.01); *A61B 18/1492* (2013.01); *G01K 7/02* (2013.01); *A61B 2017/00526* (2013.01); *A61B 2018/00077* (2013.01); *A61B 2018/00083* (2013.01); *A61B 2018/00351* (2013.01); *A61B 2018/00577* (2013.01); *A61B 2018/00821* (2013.01); *A61B 2018/00839* (2013.01); *A61B 2090/065* (2016.02); *A61B 2218/002* (2013.01)

(58) Field of Classification Search
CPC ............... A61B 18/14; A61B 18/1492; A61B 2017/00526; A61B 2018/00077; A61B 2018/00083; A61B 2018/00351; A61B 2018/00577; A61B 2018/00821; A61B 2018/00839; A61B 2090/065; A61B 2218/002; G01K 7/02
See application file for complete search history.

(56) References Cited

U.S. PATENT DOCUMENTS

| | | | |
|---|---|---|---|
| 4,732,619 A | 3/1988 | Nanigian | |
| 5,111,002 A | 5/1992 | Hollander | |
| 5,391,199 A | 2/1995 | Ben-Haim | |
| 5,680,860 A * | 10/1997 | Imran | A61B 18/1492 600/374 |
| 5,769,847 A * | 6/1998 | Panescu | A61B 18/00 374/E1.005 |
| 6,064,905 A | 5/2000 | Webster et al. | |
| 6,135,953 A | 10/2000 | Carim | |

(Continued)

FOREIGN PATENT DOCUMENTS

WO 96/05768 9/1996

OTHER PUBLICATIONS

European Search Report from corresponding European Patent Application 16202498.8, dated May 8, 2017, pp. 1-8.

*Primary Examiner* — Daniel W Fowler
(74) *Attorney, Agent, or Firm* — Dergosits & Noah LLP; Todd A. Noah

(57) ABSTRACT

This disclosure is directed to an ablation electrode having a cylindrical body in which a first conducting layer has an exterior surface and an interior surface and a second conducting layer is connected to a desired position on the interior surface of the first conducting layer forming a thermocouple at the desired position.

7 Claims, 9 Drawing Sheets

(56) References Cited

U.S. PATENT DOCUMENTS

| | | | |
|---|---|---|---|
| 6,239,724 B1 | 5/2001 | Doron et al. | |
| 6,312,425 B1 * | 11/2001 | Simpson | A61B 18/1492 |
| | | | 600/549 |
| 6,332,089 B1 | 12/2001 | Acker et al. | |
| 6,400,976 B1 | 6/2002 | Champeau | |
| 6,468,260 B1 | 10/2002 | Bumbalough et al. | |
| 6,484,118 B1 | 11/2002 | Govari | |
| 6,500,167 B1 | 12/2002 | Webster et al. | |
| 6,522,933 B2 | 2/2003 | Nguyen | |
| 6,618,612 B1 | 9/2003 | Acker et al. | |
| 6,690,963 B2 | 2/2004 | Ben-Haim et al. | |
| 6,709,432 B2 | 3/2004 | Ferek-Patric | |
| 8,034,052 B2 | 10/2011 | Podhajsky | |
| 8,311,603 B2 | 11/2012 | Faernes et al. | |
| 8,747,416 B2 | 6/2014 | Hakala et al. | |
| 8,821,487 B2 | 9/2014 | Arts et al. | |
| 2002/0021743 A1 | 2/2002 | Ruppert et al. | |
| 2002/0026183 A1 | 2/2002 | Simpson | |
| 2002/0065455 A1 | 5/2002 | Ben-Haim | |
| 2002/0072738 A1 * | 6/2002 | Edwards | A61B 18/1485 |
| | | | 606/41 |
| 2003/0120150 A1 | 6/2003 | Govari | |
| 2004/0068178 A1 | 4/2004 | Govari | |
| 2006/0100618 A1 * | 5/2006 | Chan | A61B 18/1492 |
| | | | 606/41 |
| 2007/0250055 A1 | 10/2007 | Johnson et al. | |
| 2009/0240249 A1 | 9/2009 | Chan et al. | |
| 2012/0143088 A1 | 6/2012 | Schultz | |
| 2012/0172857 A1 * | 7/2012 | Harrison | A61B 18/1477 |
| | | | 606/33 |
| 2014/0261985 A1 * | 9/2014 | Selkee | A61M 25/0009 |
| | | | 156/187 |
| 2014/0305699 A1 | 10/2014 | Govari et al. | |
| 2014/0309512 A1 | 10/2014 | Govari et al. | |

\* cited by examiner

MULTILAYER SPLIT ABLATION ELECTRODE

FIELD OF THE PRESENT DISCLOSURE

This invention relates to electrophysiologic (EP) catheters, in particular, to sensing the temperature of EP electrodes for ablation of the heart.

BACKGROUND

Electrophysiology catheters are commonly used for mapping electrical activity in the heart. Various electrode designs are known for different purposes. Certain types of electrical activity within a heart chamber are not cyclical. Instead of regular, coordinated electrical activity, disorganized electrical signals may impede heart function. Such electrical activity is random from beat to beat. An example is atrial fibrillation, which results from improper control of the timing and sequence of muscle contractions associated with a heartbeat. Other examples include arterial flutter or arterial fibrillation, and ventricular tachycardia originating in scars in the wall of the ventricle that have resulted from infarcts.

Suitable treatments may include performing an ablation procedure, such as targeted ablation of myocardial tissue to treat the cardiac arrhythmias. One specific type of an ablation procedure is termed pulmonary vein isolation, in which tissue in the area adjacent the junction of the pulmonary veins and the left atrium is ablated. In such treatments, to reduce fibrillation or other arrhythmias, radiofrequency energy may be delivered by an ablation electrode to pulmonary vein tissue in order to create one or more lesions to block electrical conduction and to electrically isolate certain areas. This isolation may minimize the migration of irregular electrical activity to other areas of the heart. To deliver the radiofrequency energy to ablate tissue and thereby form conduction blocking lesions one or more ablation electrodes may be brought into contact or close proximity with atrial and pulmonary vein tissue.

A catheter may be used to position the ablation electrode to apply RF energy and create a lesion to break arrhythmogenic current paths in the cardiac tissue. It is desirable to know the temperature of the ablation electrode to prevent heating the tissue excessively. Current ablation electrodes may be equipped with thermocouples, but due to the size of current thermocouples in relation to the catheter and ablation electrode the thermocouple is usually attached at an edge of the ablation electrode (also "ring electrode") rather than at a central (or "focal") band of the electrode. The temperature at the edge of an ablation electrode may be significantly different from the temperature at the central band. Furthermore, and particularly when the ablation electrode is positioned correctly, the edge of the ablation electrode may be less likely to be in contact with the tissue being ablated. A temperature difference may also be accentuated in longer (e.g., 8 mm) ablation electrodes. For these and other applications, it would be desirable to determine the temperature of an ablation electrode at the point of contact with tissue as accurately as possible to avoid excess heating, or even charring, of the tissue. Accordingly, the embodiments of this disclosure as described in the following materials satisfy these and other needs.

SUMMARY

The present disclosure is directed to a ring ablation electrode. In an embodiment, a ring ablation electrode is substantially cylindrical with proximal and distal ends and at least one lumen running through the body. The ring electrode has a first layer of a first conducting material, an electrically insulating layer, and a second layer of a second conducting material different from the first conducting material. In the ring electrode, the first layer is substantially cylindrical and the first and second layers are in electrically conductive contact at a contact point forming a thermocouple. The thermocouple is positioned on the first layer to measure a temperature of a region of the cylindrical body, where the region centrally-located between the proximal and distal ends of the cylindrical body. Further, the electrically insulating layer is between the first and second layers except for at least the contact point.

In an embodiment, a method for forming a thermocouple on an electrode for an ablation catheter includes the following steps. First, designating a contact point on a first layer, where the first layer is made of a first conducting material. Second, adding an insulating layer to the first layer except for at least the contact point, where the insulating layer is made of an electrically insulating material. Third, adding a second layer to the insulating layer and the contact point, where the second layer is made of a second conducting material that is different from the first conducting material, where the second layer is added to the contact point in a way that makes in electrical contact with the first layer, where the first layer, insulating layer, and second layer form a malleable plate, and where the thermocouple includes the first layer, the second layer, and the contact point. Fourth, attaching a lead wire to the second layer. And fifth, shaping the malleable plate into an electrode for an ablation catheter.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Figure 1:
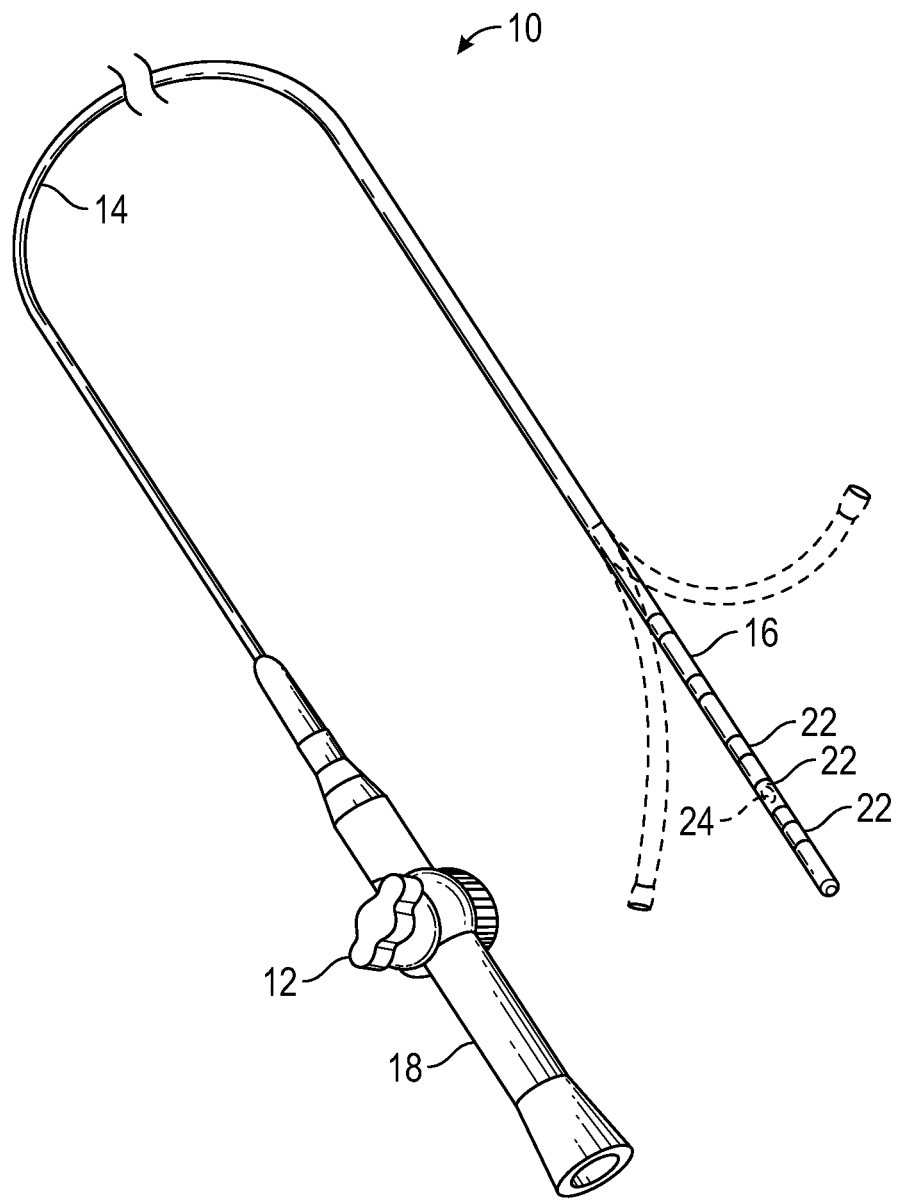
FIG. 1 is a top plan view of a catheter equipped with multiple ring electrodes, according to one embodiment.

In one or more embodiments, to determine the temperature of a ring electrode at the region of contact with tissue as accurately as possible a thermocouple is formed on the ring electrode at or sufficiently near the region of tissue contact. These embodiments use the surface material of the ablation electrode as a first conductive element of the thermocouple. To form the thermocouple, a second conductive element of different conductivity is connected to the first conductive element. To position the thermocouple at or sufficiently near the region of tissue contact, the second conductive element is connected to the back side of the surface material within the area on the backside of the surface material that is opposite to the region of tissue contact. In other words, a region of the "top" surface of the surface material will contact tissue. This contacting region on the top surface will have a corresponding region on the "bottom" surface of the surface material. And the second element will be connected on the "bottom" surface of the surface material at or sufficiently near the corresponding region so that the temperature sensed by the thermocouple is representative of the temperature of the ring electrode where the ablation electrode is in contact with tissue. Embodiments with this construction will be described further with reference to FIGS. 2-14. FIGS. 1 and 15 provide further context for the use of embodiments of a ring electrode.

FIG. 1 is a top plan view of a catheter 10 equipped with ring electrodes 22, according to one embodiment. As shown in FIG. 1, catheter 10 comprises an elongated catheter body 14 having proximal and distal ends and a control handle 18 at the proximal end of catheter body 14, with one or more ring electrodes 22 mounted at the distal end of catheter body 14. Ring electrodes 22 are also adapted for contact with target tissue. In this embodiment, each ring electrode 22 may be equipped with one or more thermocouples (e.g., thermocouples 50, 52, FIG. 5) for sensing a temperature of ring electrode 22.

Catheter body 14 comprises an elongated tubular construction having a single, axial, or central lumen (not shown), but can optionally have multiple lumens if desired. Ring electrodes 22 may also be provided to form a blocking lesion. The number of ring electrodes 22 may vary depending on the design of catheter 10. In the embodiment, three ring electrodes 22 are shown. In another embodiment, catheter body 14 includes one ring electrode 22. In some embodiments, a lumen (not shown) within catheter body 14 may be used to supply a suitable irrigation fluid, such as heparinized saline, to ring electrodes 22. A fitting (not shown) in the control handle 18 may be provided to conduct irrigation fluid from a suitable source or pump into the lumen.

In one embodiment, intermediate section 16 may be uni- or bi-directionally deflectable off-axis from the catheter body, as indicated, to provide the arc needed to position the electrodes to ablate the tissue in an arcuate pattern. Proximal of catheter body 14 is control handle 18 that allows an operator to maneuver the catheter, which may include deflecting intermediate section 16 when a steerable embodiment is employed. In an example, control handle 18 may include deflection knob 12 that is pivoted in a clockwise or counterclockwise direction for deflection in the respective direction. In other embodiments, other steerable designs may be employed, such as the control handles for manipulating multiple control wires as described, for example, in U.S. Pat. Nos. 6,468,260, 6,500,167, and 6,522,933 and U.S. Patent Publication No. 2012/0143088, filed Dec. 3, 2010, the entire disclosures of which are incorporated herein by reference.

The catheter body 14 is flexible, i.e., bendable, but substantially non-compressible along its length. The catheter body 14 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 14 so that, when the control handle 14 is rotated, the intermediate section distal end of the catheter body will rotate in a corresponding manner. The outer diameter of the catheter body 14 is not critical, but generally should be as small as possible and may be no more than about 10 french depending on the desired application. Likewise the thickness of the outer wall is not critical, but may be thin enough so that the central lumen can accommodate a puller wire, lead wires, sensor cables and any other wires, cables, or tubes. If desired, the inner surface of the outer wall is lined with a stiffening tube (not shown) to provide improved torsional stability. An example of a catheter body construction suitable for use in connection with the disclosed subject matter is described and depicted in U.S. Pat. No. 6,064,905, the entire disclosure of which is incorporated herein by reference.

The following is an exemplary use of a catheter with an ablation electrode. An electrophysiologist may introduce a guiding sheath, guidewire and dilator into the patient, as is generally known in the art, such as by the Seldinger technique that provides access for an introducer sheath through a peripheral vein, typically a femoral vein. Other suitable approaches include accessing the left atrium via the superior vena cava, or use of a retrograde intra-arterial technique. Examples of suitable guiding sheaths for use in connection with the catheter are the PREFACE™ Braided Guiding Sheath (commercially available from Biosense Webster, Inc., Diamond Bar, Calif.) and the DiRex™ Guiding Sheath (commercially available from BARD, Murray Hill, N.J.). The guidewire is inserted, the dilator is removed, and the catheter body 12 is introduced through the guiding sheath whereby the guidewire lumen in the expander permits the catheter to pass over the guidewire. In one exemplary procedure, the catheter is first introduced to the right atrium (RA) via the inferior vena cava (IVC), where it passes through a puncture in the fossa ovalis of the interatrial septum (S) in order to reach the left atrium (LA).

Accordingly, sensing electrodes (not shown) may be used to record electrical activity associated with the pulmonary vein, to identify tissue to be ablated, for example. Ring electrodes 22 may be used to create lesions to electrically isolate the pulmonary vein from the left atrium. The placement and number of ring electrodes 22 may be adapted to bring them into contact with desired areas of tissue, based on the anticipated position of the distal end of catheter 10 relative to the treatment area. For example, in one embodiment, a single ring electrode 22 may be positioned at the distal end limit of catheter 10. Also, for example, multiple ring electrodes 22 may be positioned relatively more proximally along catheter body 14.

A thermocouple (e.g., FIG. 5, thermocouple 50) is positioned within ring electrode 22 to sense the temperature of a central region 24 (described further with reference to FIG. 12) of ring electrode 22. The thermocouple is preferably sufficiently distanced from both the proximal and distal end of ring electrode 22 so that the temperature sensed by the thermocouple is highly representative of the central region of ring electrode 22. The entire surface of ring electrode 22 is actively heated, but determining the temperature of central region 24 is desired because a band of ring electrode 22 that includes central region 24 is the area of ring electrode 22 that is more likely to be in contact with the heart tissue during an ablation procedure. Furthermore, thermal energy is conducted away from ring electrode 22 in the proximal and distal directions and into catheter body 14. Irrigation and bodily fluids may also work to reduce the temperature of the proximal and distal ends of ring electrode 22 with respect to central region 24. Thus, a thermocouple positioned at a proximal or distal edge or end of ring electrode 22 may give an inaccurate or false reading. Therefore, positioning a thermocouple to sense the temperature of central region 24 may provide more accurate information regarding the temperature of the "working section" of ring electrode 22, which in turn may provide for more accurate ablation of the heart tissue.

Figure 2:
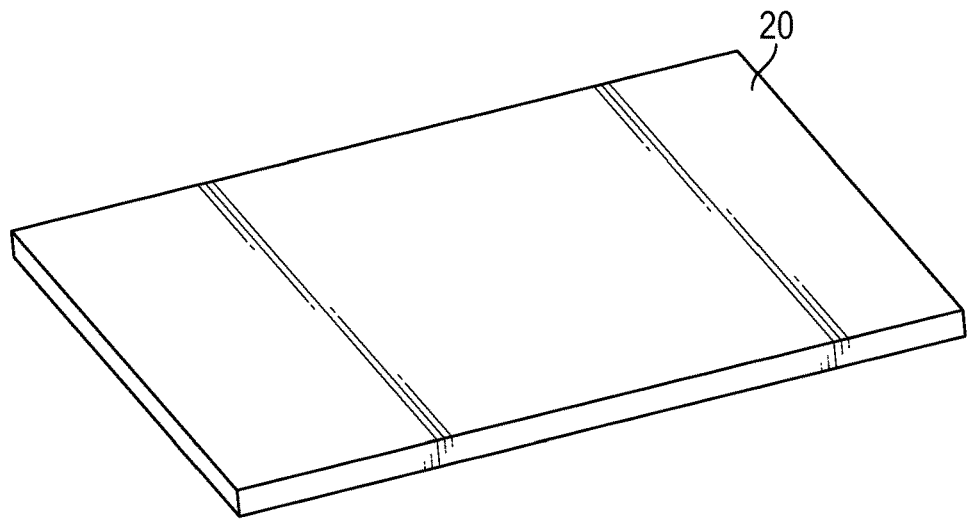
FIG. 2 is a perspective view of a plate for ring electrode, according to one embodiment.

The construction of embodiments of an ablation electrode will now be discussed further with reference to FIGS. 2-14. FIG. 2 is a perspective view of a base plate 20 that may be formed into a cylindrical ring electrode 22, according to a number of embodiments. Base plate 20 is a conductive material, commonly platinum, though other conductive materials (e.g., gold) are allowed that provide for supplying radio frequency energy to ablate tissue and that also serve as a conductor in a thermocouple. Base plate 20 may be composed of a malleable material for reasons that will be discussed further, but which mainly derive from their ability to form base plate 20 into a different shape, i.e., a cylinder, without base plate 20 becoming structurally unstable. In the embodiment, base plate 20 is dimensioned as needed to provide for being combined with other materials and formed into the final dimensions of the cylindrical ring electrode 22.

Figure 3:
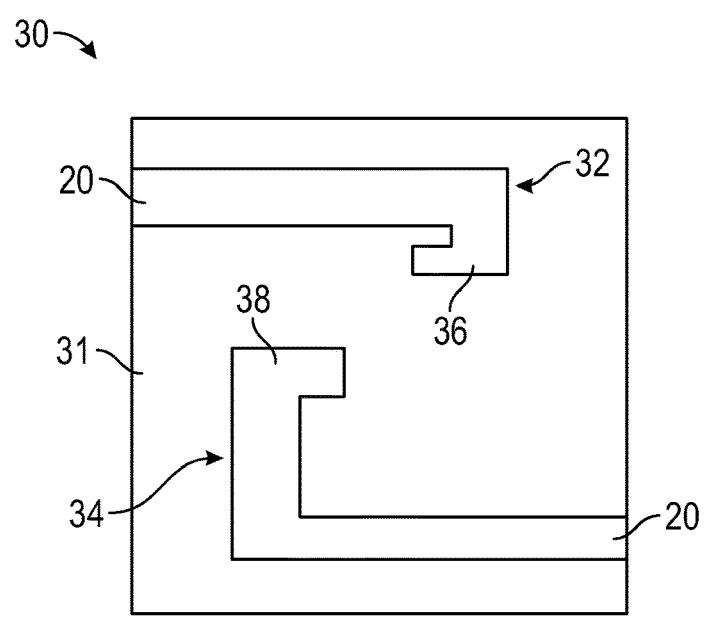
FIG. 3 is a top view of a plate for a ring electrode, according to one embodiment.

FIG. 3 is a top view of a multilayer plate 30 for an ablation electrode, according to one embodiment. In FIG. 3, base plate 20 has been partially covered by insulator 31 leaving "J-shaped" openings 32, 34 of exposed base plate 20. This "top" view of multilayer plate 30 shows surfaces that will not be in contact with tissue. Rather, in the embodiment, the "bottom" of multilayer plate 30 will be the surface that will make contact with tissue. Openings 32, 34 extend from the edge of multilayer plate 30 toward the central region. Openings 32, 34 provide areas for eventually attaching lead wires (not shown) to base plate 20. Opening 32 has a tip section 36 and opening 34 has a tip section 38. As will be discussed, the positions of tip sections 36 and 38 determine where temperature will be sensed on base plate 20. It is preferable to dimension and position tip sections 36 and 38 so that thermocouples are positioned where desired on base plate 20 and dimension and position the remainder of openings 32, 34 and so that lead wires (not shown) may be attached where desired on base plate 20. Otherwise, openings 32, 34 may be arbitrarily shaped.

Insulator 31 may be, for example, polytetrafluoroethylene (PFTE) or polyether ether ketone (PEEK). Insulator 31 may be applied using known methods. For example, insulator 31 may be insert molded (or overmolded) onto base plate 20. Insulator 31 may be pre-formed and applied as a sheet to base plate 20. Insulator 31 may also be applied to base plate 20 using physical vapor deposition. A benefit of applying insulator 31 using vapor deposition is that a very thin layer of insulator 31 may be applied, which, in turn, reduces the overall thickness of ring electrode 22. Since in the embodiment base plate 20 will eventually be formed into a cylindrical ring electrode 22, the method of applying insulator 31 and the material itself may be chosen to result in multilayer plate 30 maintaining the malleable nature of base plate 20.

Figure 4:
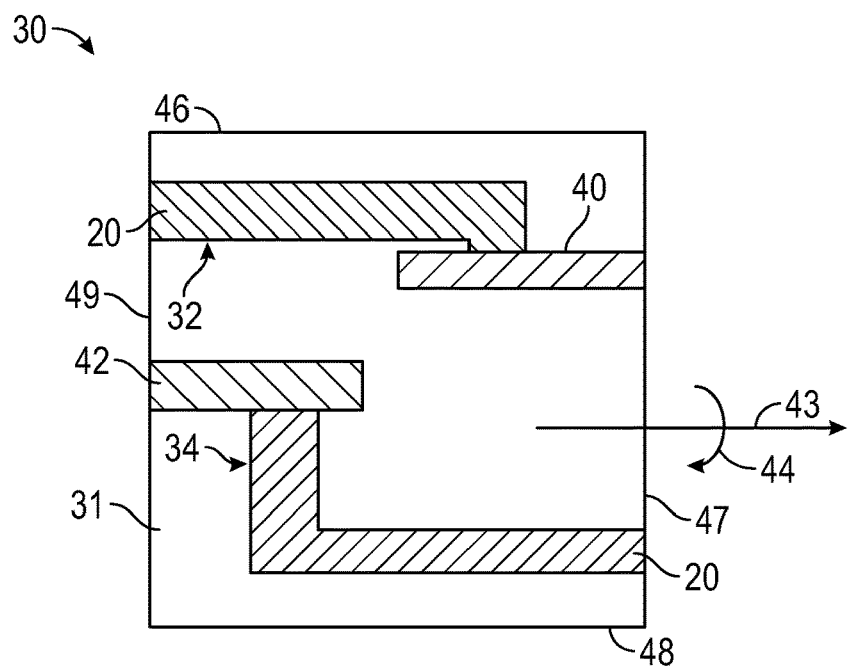
FIG. 4 is a top view of a plate for ring electrode, according to one embodiment.

FIG. 4 is a top view of the multilayer plate 30 for an ablation electrode, according to one embodiment. In FIG. 4, thermocouple layers 40, 42 have been applied over insulator 31 and connected to the base plate 20 at tip sections 36 and 38. Thermocouple layer 40 extends from the central region of base plate 20 to edge 47. Thermocouple layer 42 extends from the central region to edge 49. Thus, lead wire connections to base plate 20 may be made along the exposed sections of openings 32, 34, on the other "bottom" surface of base plate 20, and on the exposed edges 46, 47, 48, 49 of base plate 20. Similarly lead wire connections to thermocouple layers 40, 42 may be made along layers 40, 42, including where layers 40, 42 are in proximity to edges 47, 49, respectively.

Thermocouple layers 40, 42 may be composed of constantan or any nickel alloy thermocouple material—that is, layers 40, 42 may be composed of a material, which when connected to the material of base plate 20 creates a thermocouple at the connection point. By being applied over insulator 31 and selectively connected to tip sections 36 and 38, thermocouple layers 40, 42 create thermocouples at the tip sections 36 and 38 by way of being connected to a material of dissimilar conductivity. Thus, the position of the contact between the base plate 20 and the thermocouple layer, e.g., layer 40, determines where on base plate 20 the thermocouple is positioned and, since base plate 20 is eventually formed into ring electrode 22, where on ring electrode 22 the thermocouple will sense temperature.

As with insulator 31, thermocouple layers 40, 42 may be applied using known methods. Applying thermocouple layers 40, 42 using physical vapor deposition would have the same beneficial result that layers 40 and 42 may be very thin and the overall thickness of ring electrode 22 is reduced. Also as with insulator 31, the method of applying layers 40 and 42 and the material itself may benefit if they result in multilayer plate 30 maintaining the malleable nature of base plate 20. However, the chosen geometry of thermocouple layers 40, 42 may mean that thermocouple layers 40, 42 are deformed less than insulator 31 during the formation of the final shape of ring electrode 22. For that reason, thermocouple layers 40, 42 may not benefit from being malleable as much as insulator 31.

An embodiment of a process for forming multilayer plate 30 may contain the following steps. In step one, a first mask is applied to base plate 20 to define J-shaped openings 32, 34 including tip sections 36, 38 (FIG. 3). In step two, insulator 31 is applied. In step three, the first mask is removed leaving J-shaped openings 32, 34 of exposed base plate 20. In step four, a second mask is applied to define thermocouple layers 40, 42. In step five, thermocouple layers 40, 42 are applied. In step six, the second mask is removed leaving thermocouple layers 40, 42. After step six, multilayer plate 30 is complete with insulator 31 between base plate 20 and thermocouple layers 40, 42 except at tip sections 36, 38 (FIG. 3). During step five of the process, thermocouples 50, 52 (FIG. 5) are formed by the application of thermocouple layers 40, 42 onto tip sections 36, 38 (FIG. 3).

The formation of the cylindrical shape of ring electrode 22 using multilayer plate 30 will now be discussed using FIG. 4. In an embodiment, to form a cylindrical ring electrode 22, multilayer plate 30 is formed (e.g., using a cold forming technique) into a cylindrical shape by bending edge 46 about axis 43 in direction 44 until edge 46 comes into proximity with edge 48. The process creates a cylindrical shape with insulator 31 and thermocouple layers 40, 42 on the interior of the cylinder. Edges 47, 49 become the circular ends of ring electrode 22. Thus, thermocouple layer 40 is more accessible near the end created by edge 47 and thermocouple layer 42 is more accessible near the end created by edge 49.

Figure 5:
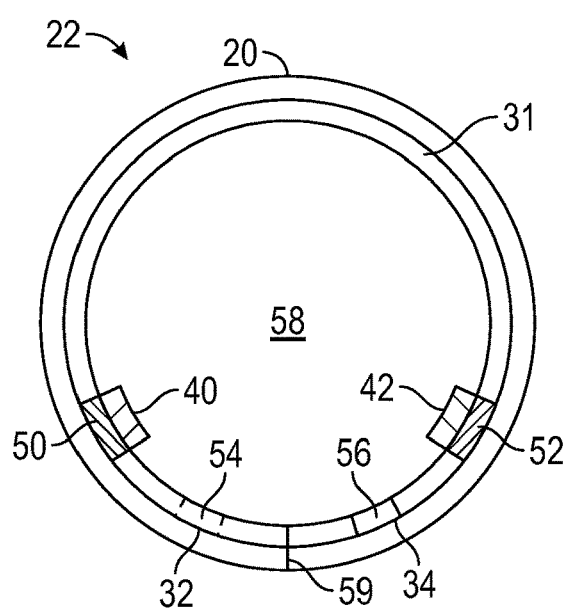
FIG. 5 is an end view of a ring electrode, according to one embodiment.

The result of forming the cylinder is discussed with reference to FIG. 5. FIG. 5 is an end view of ring electrode 22, according to one embodiment. The view is from the point of view of edge 47 of multilayer plate 30 after multilayer plate 30 is formed into a cylindrical shape in direction 44 about axis 43. In FIG. 5, edges 46, 48 have been brought together at seam 59. Base plate 20 has been formed into a cylinder, seen end-on, with insulator 31 on the inner surface of base plate 20. The formation of the cylinder created a lumen 58. By appropriately dimensioning base plate 20 and the thicknesses of insulator 31 and thermocouple layers 40, 42, lumen 58 may accommodate catheter body 12 (FIG. 1) and any elements within catheter body 12.

In FIG. 5, thermocouples 50, 52 are now shown where thermocouple layers 40, 42 come into contact with base plate 20 through insulator 31. The locations of thermocouples 50, 52 correspond to the exposed tip sections 36, 38 (FIG. 3) on base plate 20, respectively. A gap 56 in insulator 31 shows where section 34 of base plate 20 is exposed. Gap 56 provides a potential location for a connection to a lead wire. Similarly, a gap 54 in insulator 31 shows where section 32 of base plate 20 is exposed and provides a potential location for a connection to a lead wire. A benefit of gaps 54, 56 is that they provide for the attachment of lead wires to the inner surface of base plate 20, rather than the outer surface, which would cause the lead wires to come into contact with tissue. Lead wires (not shown) to base plate 20 and thermocouple layers 40, 42 may be attached before or after multilayer plate 40 is formed into a cylindrical shape.

The view in FIG. 5 depicts ring electrode 22 from a distal end (formed from edge 47) through toward a proximal end (formed from edge 49). Given such a reference, thermocouple layer 40 and section 34 extend from a central region distally and thermocouple layer 42 and section 32 extend from a central region proximally. Thus, lead wire connections for thermocouple 52 may be at opposing ends of the ring electrode 22—that is, a connection may be made to thermocouple layer 42 at the proximal end and to section 34 at the distal end. Similarly, lead wire connections for thermocouple 50 may be at opposing ends of the ring electrode 22—that is, a connection may be made to thermocouple layer 40 at the distal end and to section 32 at the proximal end.

Furthermore, since base plate 20 is exposed on its now-outer surface and at each end for the thickness of base plate 20, lead wire connections to sections 32, 34 may instead be replaced by connections to alternate, exposed areas of base plate 20 according to design criteria. If such alternate connections to base plate 20 are chosen, gaps 54 and 56 become unnecessary and (with reference to FIG. 2), it may be chosen to apply insulator 31 to all but tip sections 36, 38 of base plate 20.

In embodiments, seam 59 may be mated, i.e., mechanically or chemically joined using, e.g., a weld or adhesive to complete the circle. Seam 59 may be left unmated to accommodate expansion from within the diameter of ring electrode 22. Seam 59 may also include a gap between edges 46, 48.

In the embodiment of FIG. 5, section 32 extended in the proximal direction and thermocouple layer 40 extended in the distal direction from the central region of ring electrode 22. This arrangement provided for connecting lead wires to thermocouple 50, one at each end of ring electrode 22. It may be desirable to provide for connecting lead wires to thermocouple 50 where both lead wires are at the same end of ring electrode 22.

Figure 6:
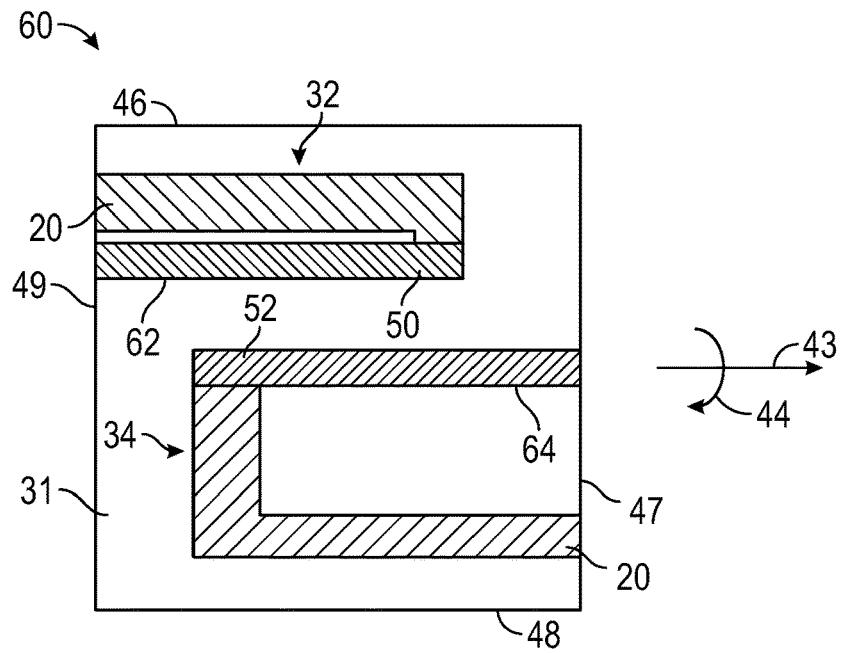
FIG. 6 is a top view of a plate for a ring electrode, according to one embodiment.

FIG. 6 is a top view of a multilayer plate 60 for an ablation electrode, according to one embodiment. In this embodiment, thermocouple layers 62, 64 are applied to tip sections 36, 38 (FIG. 3) to form thermocouples 50, 52 (FIG. 5) respectively. Thermocouple layer 62 is positioned on multilayer plate 60 so that both section 32 and thermocouple layer 62 extend toward the same end of multilayer plate 60. Similarly, thermocouple layer 64 is positioned on multilayer plate 60 so that both section 34 and thermocouple layer 64 extend toward the same end of multilayer plate 60. In this way, lead wires for thermocouple 50 may be attached to section 32 and to thermocouple layer 62 at the same end of ring electrode 22. And lead wires for thermocouple 52 may be attached to section 34 and to thermocouple layer 64 at the same end of ring electrode 22.

Figure 7:
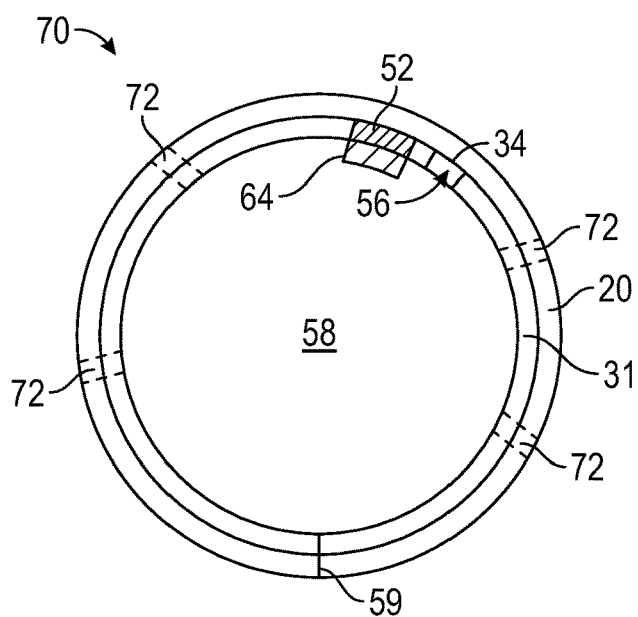
FIG. 7 is an end view of a ring electrode, according to one embodiment.

FIG. 7 is an end view of an ablation electrode 70, according to one embodiment. Ablation electrode 70 results from the formation of a cylindrical shape from multilayer plate 60 (FIG. 6), just as ring electrode 22 (FIG. 5) resulted from forming multilayer plate 30 (FIG. 4) into a cylindrical shape. The view is from the point of view of edge 47 of multilayer plate 60 after multilayer plate 60 is formed into a cylindrical shape in direction 44 about axis 43. FIG. 7 does not depict thermocouple 50, thermocouple layer 62, or section 32 from FIG. 6 to more clearly illustrate that both thermocouple layer 42 and section 34 extend to the same end of ablation electrode 70 and to illustrate that an embodiment may have only a single thermocouple. In FIG. 7, ablation electrode 70 includes irrigation holes 72, which allow irrigation fluid to pass between the inner and outer surfaces of ablation electrode 70. Irrigation holes 72 may be created in ablation electrode 70 after, or before, multilayer plate 60 is formed into the cylindrical shape. Irrigation holes 70 may be made by, for example, laser machining. Also, the number of irrigation holes 70 shown is exemplary. Irrigation holes 70 may number 8 (FIG. 10), 12 (FIG. 12), or perhaps 50, depending on the amount and type of irrigation desired.

In FIG. 7, edges 46, 48 have been brought together at seam 59. Base plate 20 has been formed into a cylinder, seen end-on, with insulator 31 on the inner surface of base plate 20. Thermocouple 52 is now shown where thermocouple layer 64 comes into contact with base plate 20 through insulator 31. The location of thermocouple 52 corresponds to the exposed tip section 38 (FIG. 3) on base plate 20, respectively. A gap 56 in insulator 31 shows where section 34 of base plate 20 is exposed and provides a potential connection for a lead wire.

The view in FIG. 7 may be considered to show ablation electrode 70 from a distal end (formed from edge 47) through toward a proximal end (formed from edge 49). Given such a reference, both thermocouple layer 64 and section 34 extend from a central region distally. Thus, lead wire connections for thermocouple 52 may be at the same end of ablation electrode 70—that is, a connection may be made to thermocouple layer 64 and to section 34 at the distal end.

Furthermore, since base plate 20 is exposed on its now-outer surface and at each end for the thickness of base plate 20, lead wire connections to section 34 may instead be replaced by connections to alternate, exposed areas of base plate 20 according to design criteria. If such alternate connections to base plate 20 are chosen, gap 56 becomes unnecessary and (with reference to FIG. 2), it may be chosen to apply insulator 31 to all but tip section 38 of base plate 20.

It should be recognized that the shapes of sections 32, 34 (FIG. 3) are arbitrary. It should also be recognized that tip sections 36, 38 (FIG. 3) are positioned on base plate 20 to set the eventual position of the corresponding thermocouples 50, 52. Other shapes for open sections are envisioned that accomplish the same positioning goal. Such shapes include, for example, the shapes depicted in FIGS. 8a-9b. Except for the shapes depicted, FIGS. 8a-9b may be constructed as described with reference to earlier figures.

Figure 8A:
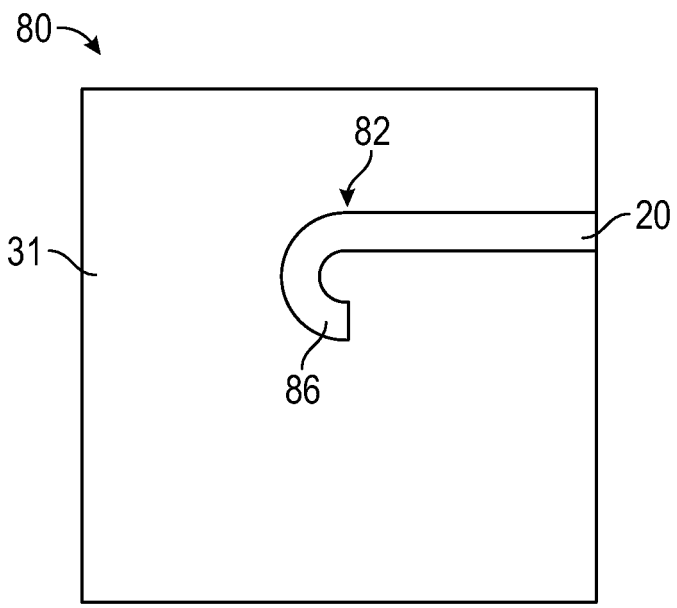
FIG. 8a is a top view of a plate for a ring electrode, according to one embodiment.
Figure 8B:
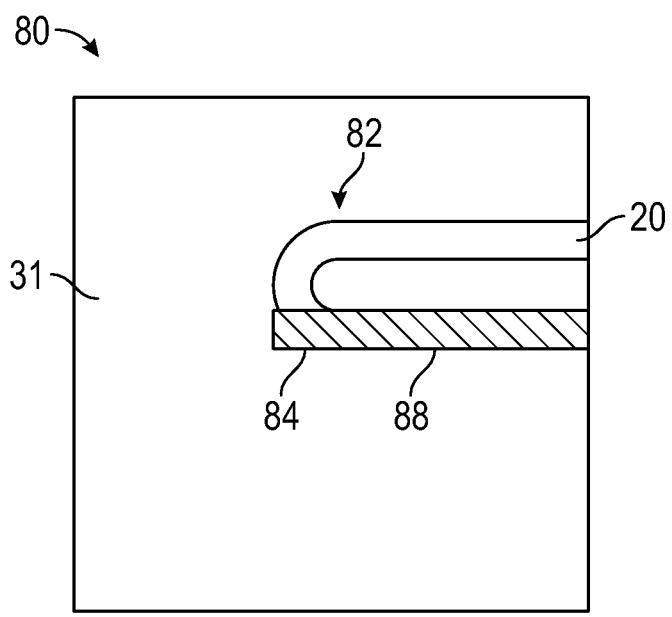
FIG. 8b is a top view of a plate for a ring electrode, according to one embodiment.

FIGS. 8a and 8b depict top views of a multilayer plate 80 for an ablation electrode, according to one embodiment. In FIG. 8a, insulator 31 has been applied to base plate 20 leaving "U-shaped" open section 82 with tip section 86. In FIG. 8b, thermocouple layer 88 has been applied to tip section 86 and atop insulator 31 to create thermocouple 84. Thermocouple 84 is created by the contact between tip section 86 and the section of thermocouple layer 88 that overlaps tip section 86. Multilayer plate 80 may be formed into a cylindrical shape with both open section 82 and thermocouple layer 88 accessible at the same end of the cylindrical shape for the attachment of lead wires.

Figure 9A:
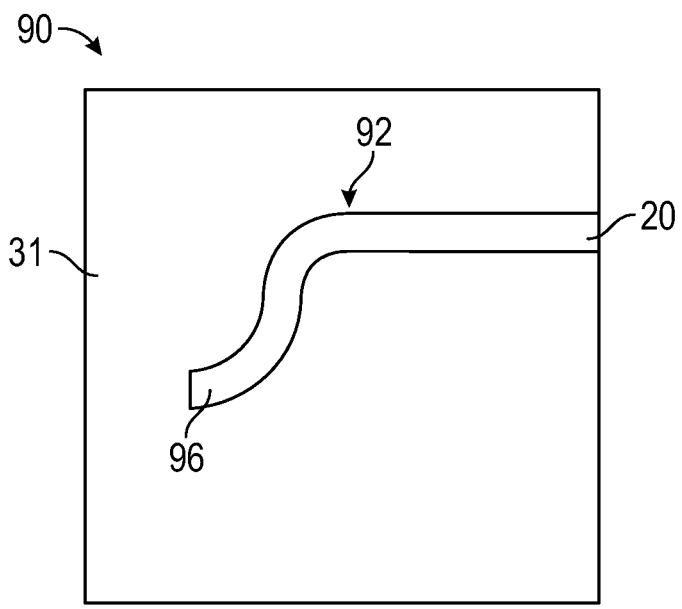
FIG. 9a is a top view of a plate for a ring electrode, according to one embodiment.
Figure 9B:
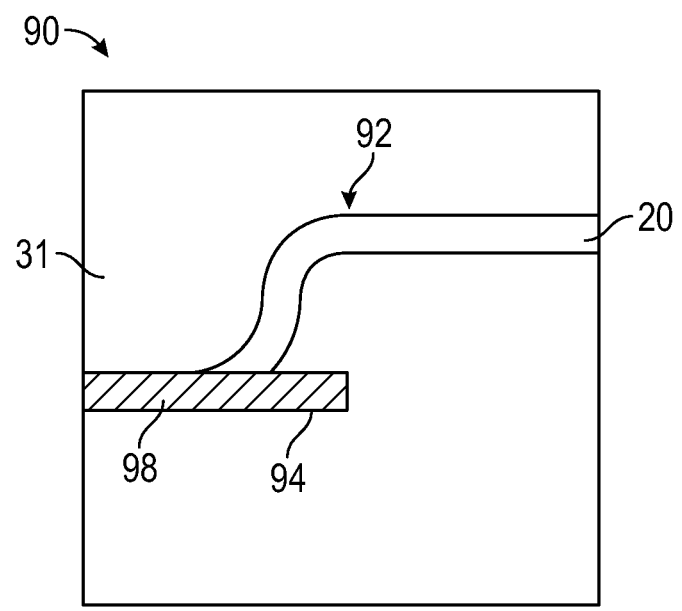
FIG. 9b is a top view of a plate for a ring electrode, according to one embodiment.

FIGS. 9a and 9b depict top views of a multilayer plate 90 for an ablation electrode, according to one embodiment. In FIG. 9a, insulator 31 has been applied to base plate 20 leaving "S-shaped" open section 92 with tip section 96. In FIG. 9b, thermocouple layer 98 has been applied to tip section 96 and atop insulator 31 to create thermocouple 94. Thermocouple 94 is created by the contact between tip section 96 and the section of thermocouple layer 98 that overlaps tip section 96. Multilayer plate 90 may be formed into a cylindrical shape with open section 92 and thermocouple layer 98 accessible at different ends of cylindrical shape for the attachment of lead wires.

Figure 10:
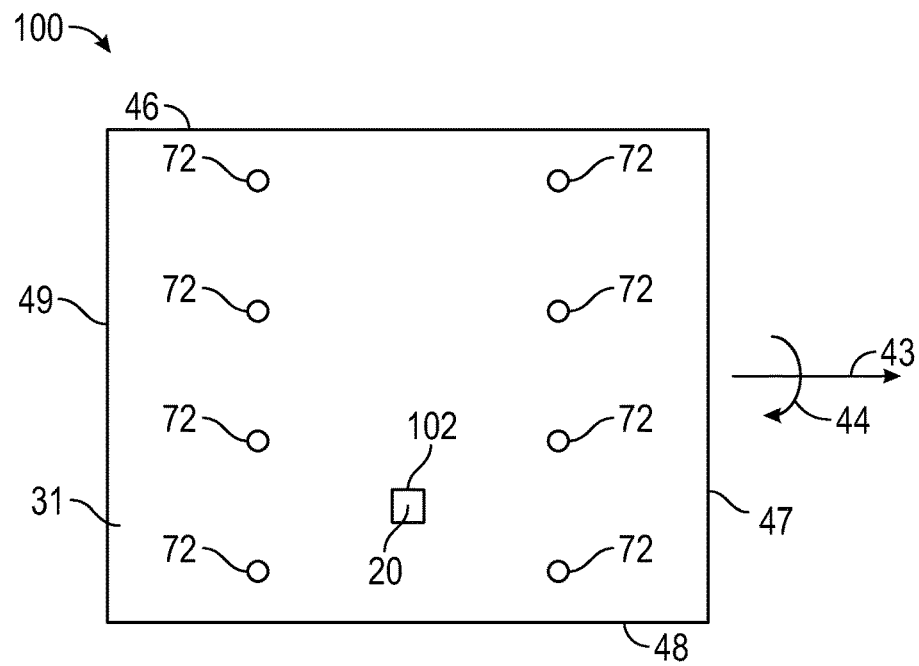
FIG. 10 is a top view of a plate for a ring electrode, according to one embodiment.

FIG. 10 is a top view of a multilayer plate 100 for an ablation electrode, according to one embodiment. Except for where the following discussion differs, the embodiments depicted in FIGS. 10-14 may be constructed as described with reference to earlier figures. In FIG. 10, base plate 20 has been partially covered by insulator 31 leaving opening 102 to exposed base plate 20. The position and dimension of opening 102 determines the position and dimension of the eventual thermocouple on multilayer plate 100, just as, for example, the positions and dimensions of tip sections 36, 38 (FIG. 3) determined the positions and dimensions of corresponding thermocouples 50, 52 (FIG. 5). Since insulator 31 covers all but opening 102 of base plate 20, a lead wire connection to base plate 20 is not available on the surface of multilayer plate 100 depicted in FIG. 10. The position of lead wires is further discussed with reference to FIGS. 11-13. In FIG. 10, multilayer plate 100 further includes irrigation holes 72, depicting an embodiment in which irrigation holes 72 are formed in multilayer plate 100 before multilayer plate 100 is formed into a final shape.

Figure 11:
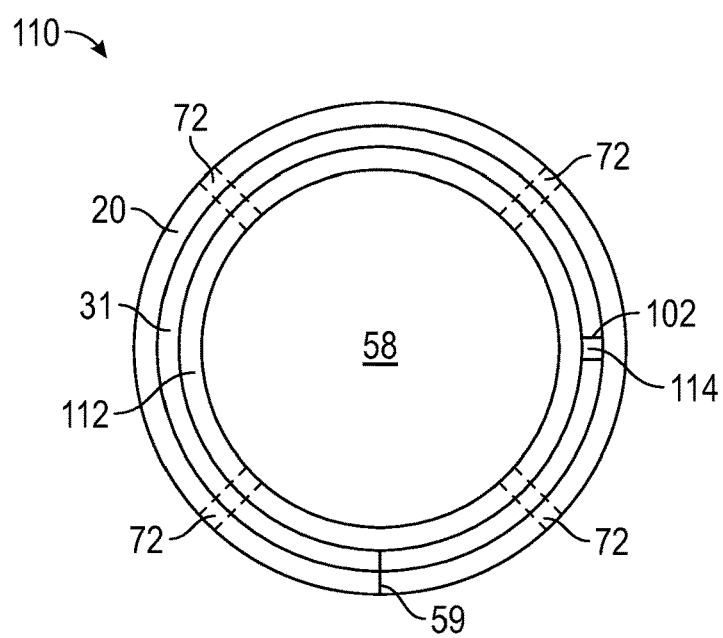
FIG. 11 is an end view of a ring electrode, according to one embodiment.

FIG. 11 is an end view of an ablation electrode 110, according to one embodiment. In FIG. 11, thermocouple layer 112 has been applied to multilayer plate 100 (FIG. 10) over insulator 31 and connected to the base plate 20 at opening 102 to form thermocouple 114. Multilayer plate 100 was then formed into a cylindrical shape by bending edge 46 about axis 43 in direction 44 until edge 46 came into proximity with edge 48. The process created a cylindrical shape with insulator 31 and thermocouple layer 112 on the interior of the cylinder. Edges 47, 49 became the circular ends of ablation electrode 110. In the embodiment, base plate 20, insulator 31, and thermocouple layer 112 form concentric cylindrical shapes, with insulator 31 inside base plate 20 and with thermocouple layer 112 inside insulator 31. Thus, the inner surface and both end thicknesses of thermocouple layer 112 are accessible for the purpose of making contact with a lead wire. Similarly, the outer surface and both end thicknesses of base plate 20 are accessible for the purpose of making contact with a lead wire.

Figure 12:
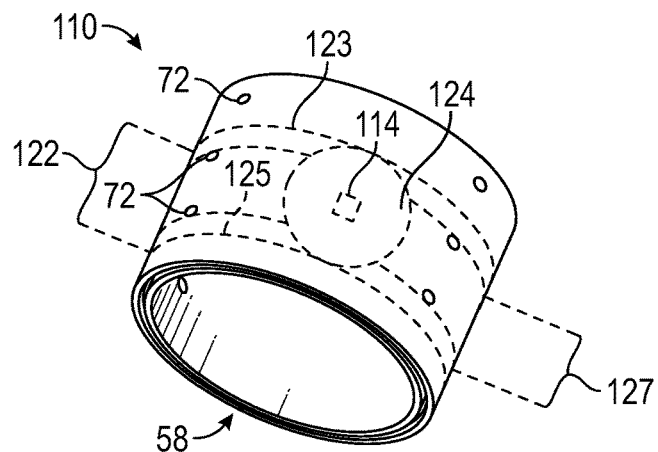
FIG. 12 is a perspective view of a ring electrode, according to one embodiment.

FIG. 12 is a perspective view of an ablation electrode 110, according to one embodiment. FIG. 12 discloses further information regarding the position of a thermocouple in embodiments of an ablation electrode. As discussed earlier with regard to FIG. 1, it is desired to sense the temperature of central region 124. Central region 124 may include part of a central band 127, where central band 127 is the area of ablation electrode 110 most likely to contact tissue during use. For that reason alone it may be desirable to measure the temperature of central band 127.

Also, as discussed earlier, due to the conduction of thermal energy away from ablation electrode 110 during use, proximal and distal bands of ablation electrode 110 may be at temperatures that are different from the temperature of the central band. That is, the proximal and distal ends of ablation electrode 110 may be at lower temperatures than central band 127. To avoid applying more heat to tissue than was intended it may also be desirable to determine the temperature of central band 127.

In that regard, in FIG. 12 a boundary 125 is located towards the proximal end of ablation electrode 110. Similarly, a boundary 123 is located towards the distal end of ablation electrode 110. Boundaries 123, 125 are not fixed locations. Rather, boundaries 123, 125 illustrate the approximate edges of a representative band 122—a band of ablation electrode 110 in which a sensed temperature is consistent. Representative band 122 includes central band 127 and representative band 122 may be larger than central band 127. But, since the temperature within representative band 122 is relatively consistent, a temperature sensed within representative band 122 may accurately represent the temperature within central band 127. Thermocouple 114 is, therefore, shown positioned between boundaries 123, 125 within representative band 122.

Further, irrigation holes 72 present a factor to be considered when positioning thermocouple 114. Irrigation holes 72 may also facilitate the loss of thermal energy from ablation electrode 110. Thus, thermocouple 114 is preferably not positioned in close proximity to any irrigation hole 72. Staying within representative band 112 while avoiding holes 72 results in thermocouple 114 being location within central region 124.

In FIG. 12, thermocouple 114 appears to be approximately equidistant from the proximal and distal ends of ablation electrode 110. However, such a location is not mandatory or necessarily even preferable. Rather, thermocouple 114 may be located arbitrarily within central region 124 since the temperature is thought to be consistent within that region. In an embodiment, thermocouple 114 may be positioned axially substantially in the center of preferred band 112 and may be positioned radially substantially in the center of the area between the axially-oriented rows of irrigation holes 72.

Figure 13:
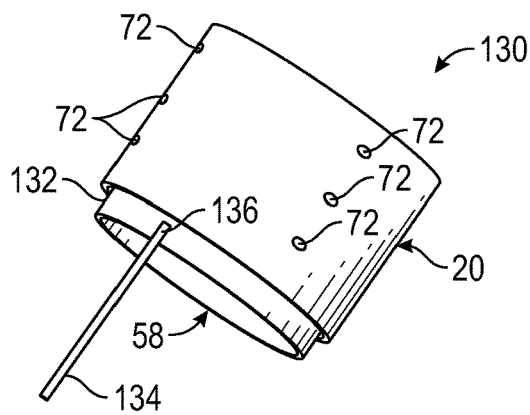
FIG. 13 is a perspective view of a ring electrode, according to one embodiment.

FIG. 13 is a perspective view of an ablation electrode, according to one embodiment. In FIG. 13, thermocouple layer 112 (FIG. 11) has been extended proximally from base plate 20 to create an exposed thermocouple layer band 132. Exposed band 132 facilitates the attachment of a lead wire 134 by presenting access for making a contact 136 to the surface of thermocouple layer 112. Contact 136 is on a surface of exposed band 132 that is exterior relative to lumen 58. This is beneficial because lumen 58 may be filled with, for example, catheter body 12.

It should be recognized that in the embodiments the relative positions of the layers of the ablation electrodes may be altered. For example, with reference to the orientation of the cylindrical layers of FIGS. 10-13, a base plate of thermocouple material may have an insulator applied to it except for an opening, with a platinum layer then applied to cover the insulator and connect to the thermocouple layer to create the thermocouple. The multilayer plate, this time with the thermocouple material on the "bottom" could be then formed into a cylindrical shape with the thermocouple material as the inner layer of the cylindrical shape. Alternatively, the multilayer plate with the thermocouple material on the "bottom" could be formed into a cylindrical shape with the thermocouple material as the outer layer of the cylindrical shape.

Embodiments are envisioned in which the multilayer plate is formed into a shape that is other than cylindrical. For example, an ablation electrode could be shaped to fit about a catheter body with a cross section that is a circle, oval, square, triangle, or rectangle, or imperfect versions of any of these. Forming such ablation electrodes may benefit from the multilayer plate being cut into a different shape before being formed into the final shape. For example, a multilayer plate (e.g., multilayer plate 30, 60, or 100) could be cut into a sector of a circle and the sector then formed into a cone for positioning at the distal tip of a catheter body. Also, a circular multilayer plate could be made and fashioned into a convex dish, perhaps, e.g., a hemisphere, and positioned at the distal tip of a catheter body.

In embodiments, the layers of the multilayer plate may be applied individually. For example, multilayer layer plate 100 (FIG. 10) may be created by cutting opening 102 in a sheet of insulator 31 and applying the sheet to base plate 20. A thermocouple layer 112 (FIG. 11) may then be applied to the surface of the insulator 31. Thermocouple 114 may then be formed by forcing thermocouple layer 112 through opening 102 and into contact with base plate 20. In an embodiment, thermocouple 114 is created by a spot weld. In an embodiment, irrigation holes 72 may be laser machined while the multilayer plate is flat and the plate cold formed into the desired final shape. In an embodiment, and with reference to FIG. 11, cylinders of the base plate 20, insulator 31 (with opening 102), and thermocouple layer 112 are formed individually. The individual layers are then assembled by sliding one within the other in the appropriate order. Thermocouple 114 is then formed by forcing thermocouple layer 112 through opening 102 and into contact with base plate 20, or by a spot weld.

Figure 14:
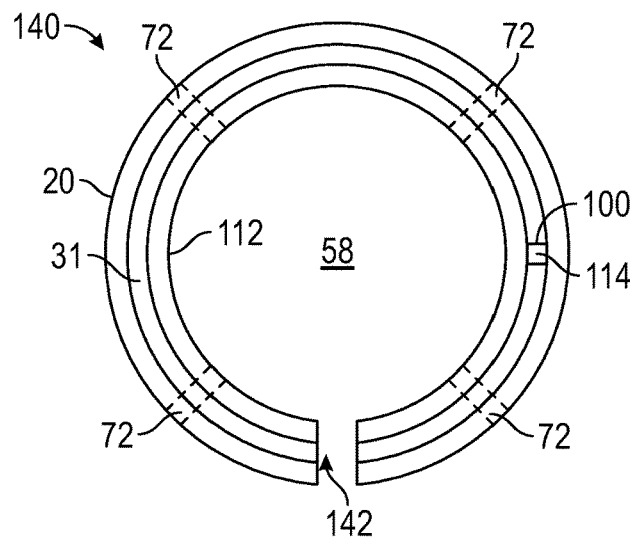
FIG. 14 is an end view of a ring electrode, according to one embodiment.
Figure 15:
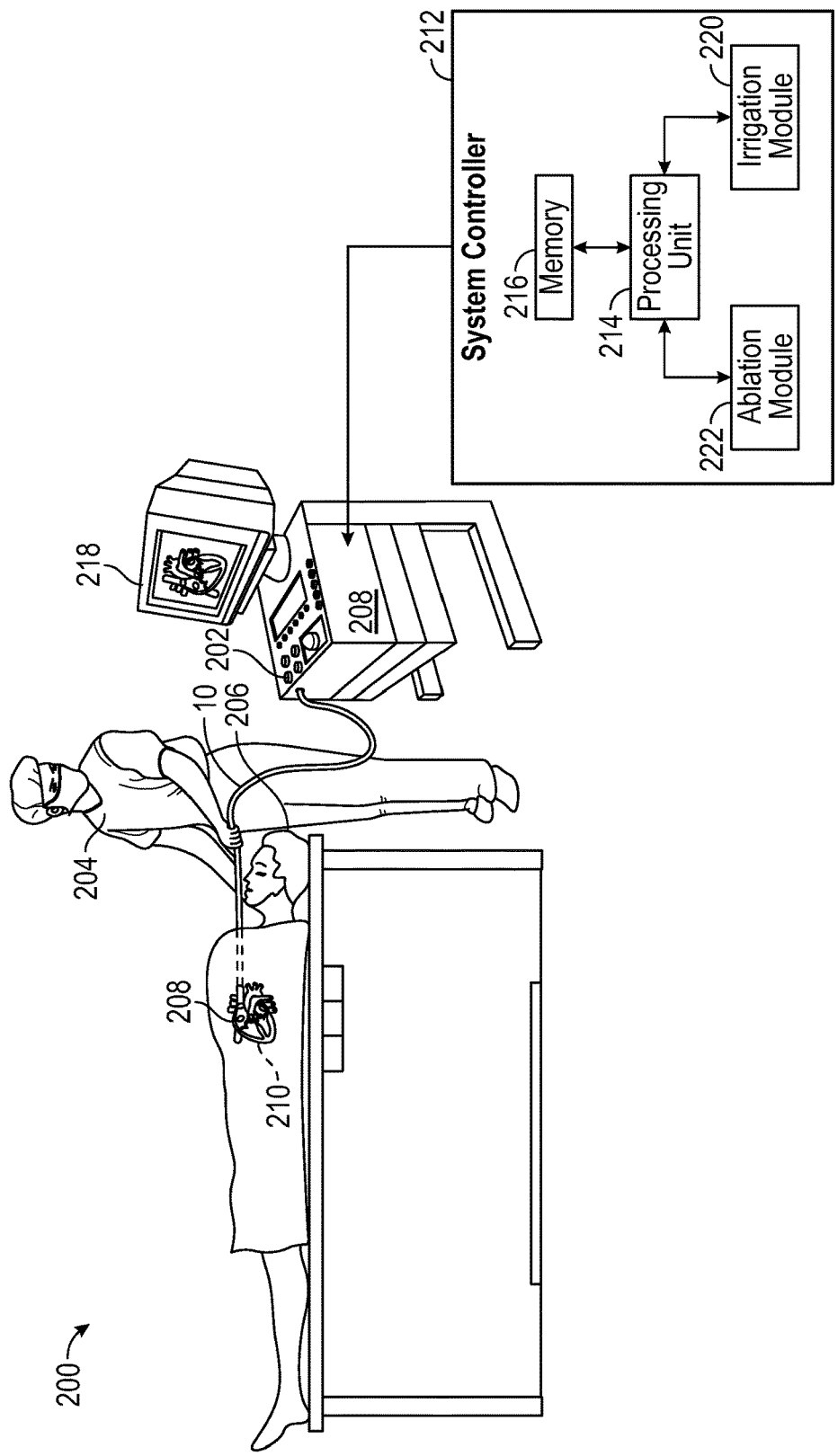
FIG. 15 is a schematic illustration of an invasive medical procedure using a catheter equipped with a ring electrode, according to one embodiment.

FIG. 14 is an end view of an ablation electrode 140, according to one embodiment. In an embodiment, ablation electrode 140 is not a complete cylinder. Ablation electrode 140 includes a gap 142. Gap 142 may be formed by, for example, a modification of the method described for forming ablation electrode 110 (FIG. 10). As described with reference to FIG. 10, seam 59 is formed when edges 46 and 48 are brought into contact to form ablation electrode 110. In the embodiment of FIG. 14, gap 142 is left in ablation electrode 140 when edges 46 and 48 are not brought into contact.

To help illustrate the use of an ablation electrode, FIG. 15 is a schematic, pictorial illustration of a system 200 for renal and/or cardiac catheterization and ablation, in accordance with an embodiment of the present invention. System 200 may be based, for example, on the CARTO™ mapping systems, produced by Biosense Webster Inc. (Diamond Bar, Calif.) and/or SmartAblate or nMarq RF generators. This system comprises an invasive probe in the form of catheter 10 with the ring electrode 22 at the distal end and a control and/or ablation console 202. An operator 204, such as a cardiologist, electrophysiologist or interventional radiologist, inserts ablation catheter 10 into and through the body of a patient 206, such as through a femoral or radial access approach, so that a distal end of catheter 10, in particular, ring electrode 22, engages tissue at a desired location or locations, such as a chamber of heart 208 of patient 206. Catheter 10 is typically connected by a suitable connector at its proximal end to console 202. Console 202 comprises a RF generator 208, which supplies high-frequency electrical energy via the catheter for ablating tissue 210 at the locations engaged by ring electrode 22.

Console 202 may also use magnetic position sensing to determine position coordinates of the distal end of catheter 10 inside the body of the patient 206. For this purpose, a driver circuit in console 202 drives field generators to generate magnetic fields within the body of patient 206. Typically, the field generators comprise coils, which are placed below the patient's torso at known positions external to the patient. These coils generate magnetic fields in a predefined working volume that contains the area of interest. A magnetic field sensor (not shown) within distal end of catheter 10 generates electrical signals in response to these magnetic fields. A signal processor in console 202 may process these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Console 202 may include system controller 212, comprising a processing unit 216 communicating with a memory 214, wherein is stored software for operation of system 200. Controller 212 may be an industry standard personal computer comprising a general purpose computer processing unit. However, in some embodiments, at least some of the functions of the controller are performed using custom designed application specific integrated circuits (ASICs) or a field programmable gate array (FPGA). Controller 212 is typically operated by the operator 204 using suitable input peripherals and a graphic user interface (GUI) 218 which enable the operator to set parameters of the system 200. GUI 218 typically also displays results of the procedure to the operator. The software in memory 214 may be downloaded to the controller in electronic form, over a network, for example. Alternatively or additionally, the software may be provided on non-transitory tangible media such as optical, magnetic or electronic storage media. In some embodiments, one or more contact force sensors may send signals to console 202 to provide an indication of the pressure on ring electrode 22. Signals from contact force sensor wires may be provided to system controller 212 to obtain measurements from strain gauge 134. Such signals may be used to provide to the physician the level of tissue contact of each individual electrode. Additionally, the system controller 212 will provide an indication as to which of the multi-electrodes are in contact with the tissue to be ablated. With this feedback information, the practitioner will be able to make the necessary adjustments to ensure a complete ablation. As noted above, this invention is well suited for any multi-electrode catheter such as, for example, those having a lasso, arcuate, helical or basket configuration of ring electrodes.

Typically, during an ablation, heat is generated by the RF energy in the tissue of the patient to effect the ablation and some of this heat is reflected to the ring electrode 22 causing coagulation at and around the electrode. System 200 irrigates this region through irrigation apertures 72 (shown in FIG. 5) and the rate of flow of irrigation is controlled by irrigation module 220 and the power (RF energy) sent to ring electrode 22 is controlled by ablation module 222. Further, the percentage of the surface of ring electrode 22 that is coupled with tissue may be estimated based on the contact force observed. As yet another example, additional sensors of catheter 10 may provide intracardiac electrocardiograms to system controller 212, to be used for determining when the tissue site being ablated is no longer conducting arrhythmogenic currents.

In a further aspect, catheter 10 may include cabling with built-in or embedded lead wires for ring electrodes 22 as described in U.S. Patent Publication No. 2014/0309512, filed Apr. 11, 2013, entitled HIGH DENSITY ELECTRODE STRUCTURE, and U.S. Patent Publication No. 2014/0305699, filed Oct. 25, 2013, entitled CONNECTION OF ELECTRODES TO WIRES COILED ON A CORE, the entire disclosures of which are hereby incorporated by reference.

The preceding description has been presented with reference to presently disclosed embodiments. Those skilled in the art and technology to which this disclosure pertains will appreciate that alterations and changes in the described structure may be practiced without meaningfully departing from the principal, spirit and scope of this disclosure. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrode for an ablation catheter, the electrode comprising a substantially cylindrical body having proximal and distal ends and at least one lumen therethrough, the substantially cylindrical body comprising:
   a first layer comprised of a first conducting material;
   an electrically insulating layer; and
   a second layer comprised of a second conducting material different from the first conducting material, wherein:
   the first layer is substantially cylindrical,
   the first and second layers are in electrically conductive contact at a contact point forming first and second thermocouples,
   the first thermocouple is positioned to measure a temperature of a first region of the cylindrical body, the first region centrally-located between the proximal and distal ends of the cylindrical body,
   the second thermocouple is positioned to measure a temperature of a second region of the cylindrical body, the second region centrally-located between the proximal and distal ends of the cylindrical body,
   the electrically insulating layer is between the first and second layers except for at least the contact point, and
   the first and second layers form a first lead wire connection at the proximal end of the cylindrical body for conductively connecting the first centrally located thermocouple and a second lead wire connection at the distal end of the cylindrical body for conductively connecting the second centrally located thermocouple.

2. The electrode of claim 1 wherein the electrically insulating layer is one or more of polytetrafluoroethylene or polyether ether ketone.

3. The electrode of claim 1, wherein the first layer comprises a substantially cylindrical outer layer and the second layer comprises a substantially cylindrical inner layer, the outer layer substantially overlapping the inner layer, and wherein a non-overlapped section of the inner layer extends from under the outer layer, the electrode further comprising a lead wire conductively attached to the non-overlapped section of the inner layer.

4. The electrode of claim 3, wherein the first layer comprises platinum and the second layer comprises constantan.

5. The electrode of claim 1, wherein the substantially cylindrical body further comprises an expandable seam running substantially longitudinally between the distal and proximal ends.

6. The electrode of claim 1, wherein the electrically insulating layer comprises material deposited onto the first layer except for the contact point, and the second layer comprises material deposited onto the electrically insulating layer and deposited onto the contact point.

7. The electrode of claim 6, wherein the second layer comprises a line trace.

* * * * *